United States Patent [19]
Mohajer

[11] Patent Number: 5,464,022
[45] Date of Patent: Nov. 7, 1995

[54] ENDOMETRIAL SAMPLER

[76] Inventor: Reza S. Mohajer, 3115 W. Shore Dr., Orchard Lake, Mich. 48033

[21] Appl. No.: 336,923

[22] Filed: Nov. 10, 1994

[51] Int. Cl.$^6$ .................................................. A61B 10/00
[52] U.S. Cl. ........................................... 128/758; 604/38
[58] Field of Search .................................... 128/749, 752, 128/758; 604/27.36, 38.54, 55, 121, 181, 264, 272, 280–283

[56] References Cited

U.S. PATENT DOCUMENTS 3,636,940   1/1972   Gravlee ..................................... 604/38
5,083,572   1/1992   Pokorny ..................................... 604/27

Primary Examiner—Max Hindenburg
Attorney, Agent, or Firm—Gifford, Krass, Groh, Sprinkle, Patmore, Anderson & Citkowski

[57] ABSTRACT

An endometrial aspirator includes hollow cylindrical tube, open at one end and including a piston therein. The piston is configured to include a tapered portion which may be projected from the open end of the tube so as to form a cervical dilator which facilitates insertion of the aspirator into the uterus.

13 Claims, 1 Drawing Sheet

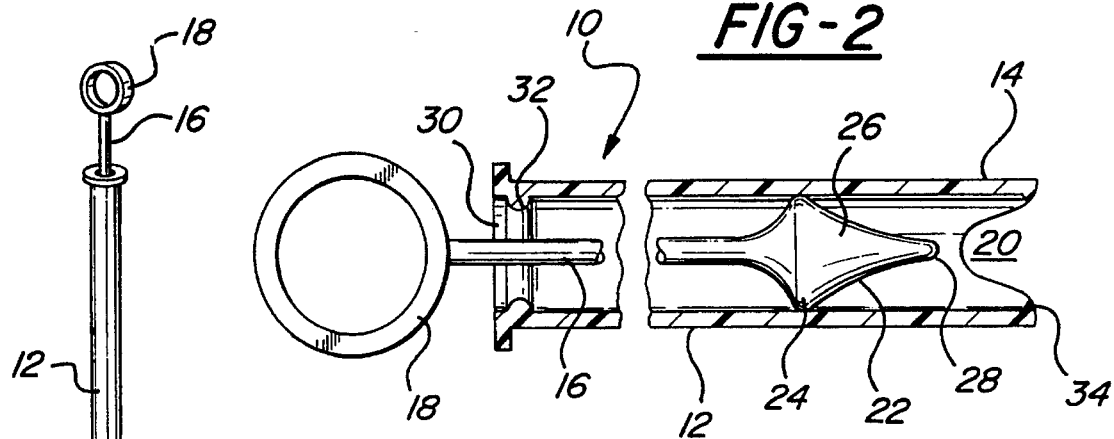
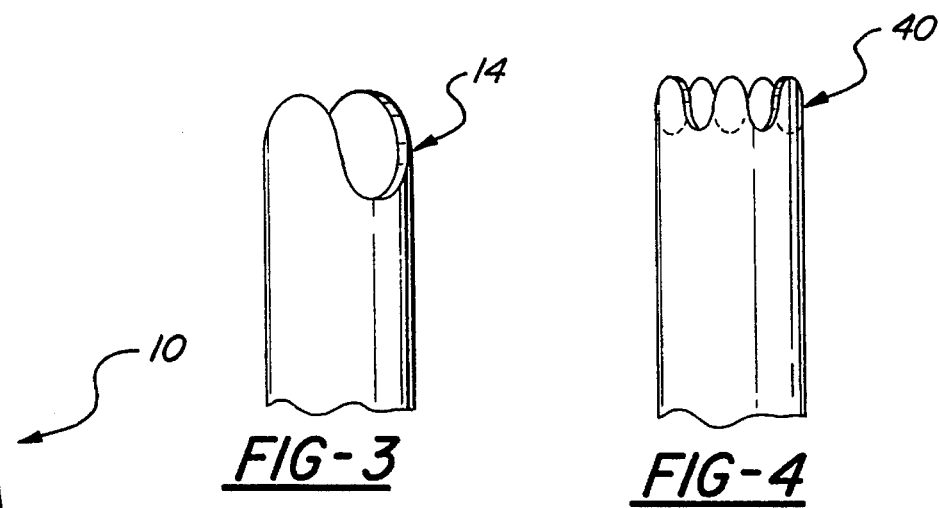
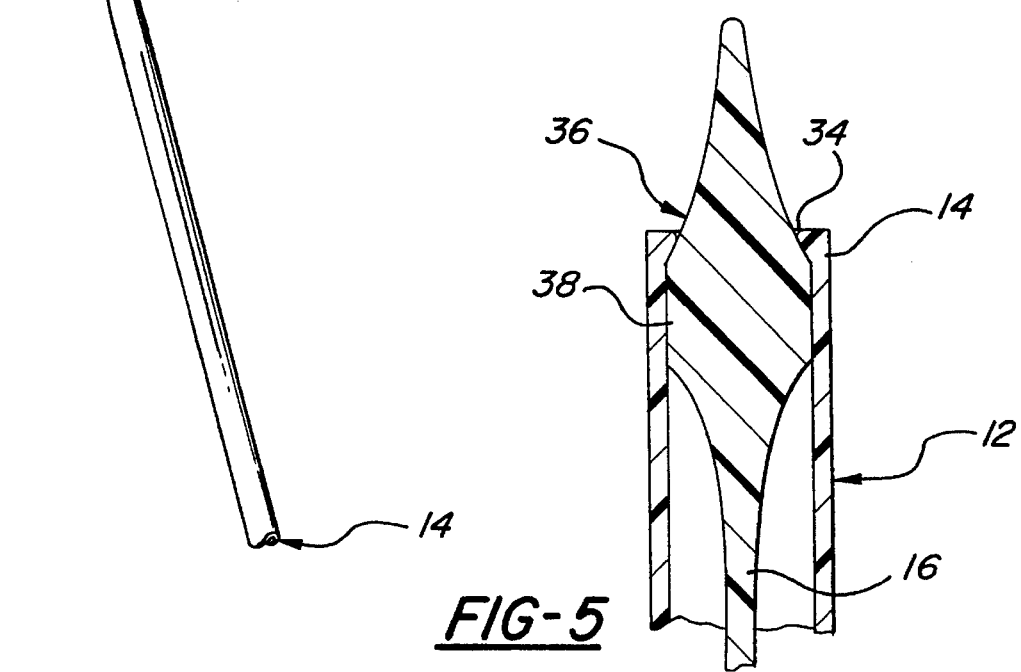

ENDOMETRIAL SAMPLER

FIELD OF THE INVENTION

This invention relates generally to devices for sampling uterine tissue. More specifically, the invention relates to a device for aspirating endometrial tissue samples.

BACKGROUND OF THE INVENTION

In many instances, it is necessary for a physician to obtain a sample of endometrial tissue from a patient. For example, endometrial samples are taken for the detection of endometrial carcinoma or precancerous conditions. Endometrial tissue is also sampled to determine response to hormone therapy and in connection with the diagnosis of pathology associated with infertility. Endometrial tissue samples are obtained by scraping the uterine wall and aspirating the removed tissue. U.S. Pat. No. 4,935,003 discloses an aspiration tip configured to be connected to an external suction source. The tip is primarily used for performing suction abortions, but may also be employed to collect endometrial samples. The tip is relatively large, as is the volume of tissue collected thereby. In most instances, a relatively small tissue sample will suffice, and in order to minimize patient discomfort it is usually desirable to employ a less invasive device.

A number of relatively small diameter self-contained aspirator devices are known in the prior art. U.S. Pat. No. 5,069,224 discloses an endometrial aspirator which is representative of those previously employed. The aspirator of the '224 Patent comprises a tube having a closed end and a side opening near the closed end for the collection of tissue. A piston is disposed in the tube and is moved along the length of the tube to create a suction which draws tissue into the opening. The aspirator is moved about in the uterus and the combination of suction and the scraping effect of the opening draws tissue into the bore of the tube. The closed end requires that the tube be cut in order to permit ejection of the tissue sample therefrom. Cutting involves an extra step, which it would be desirable to eliminate. Even more significantly, the closed end design of the prior art aspirator results in a loss of tissue sample, since some portion of the sample will always remain in the tip when it is cut away. The lost tissue represents a sample collected from a specific portion of the uterus, and in some instances, may be of critical importance. In any instance, the lost sample constitutes a decrease the net volume of tissue available for analysis, and it is clearly desirable to avoid such loss.

In some instances, difficulties are encountered in inserting prior art aspirators through the cervix. This problem often occurs when cervical stenosis is present and generally necessitates the use of a cervical dilator to locate and open the cervical os prior to insertion of the aspirator. Use of a dilator necessitates an extra step in the sampling procedure and requires the physician to stock additional supplies. Elimination of a separate dilation step is clearly desirable. Cervical stenosis is a fairly common condition and is generally the result of injury or previous surgical procedures; hence, cervical dilation is frequently required, and presently employed aspirators are very often supplied along with a separate dilator.

It will be appreciated from the foregoing that there is a need for a device for obtaining samples of endometrial tissue which minimizes the impact of the procedure on the patient, and which permits the utilization of the full volume of the collected sample. Ideally, the sample should be fully discharged from the aspirator without cutting. It is further desirable that the sampler is capable of being utilized in those instances where cervical stenosis is present without requiring any additional dilation steps and/or the use of extraneous instrumentation.

The present invention provides a self-contained aspirator device which is capable of functioning as its own cervical dilator. The device enables the ready collection and discharge of the entirety of an endometrial tissue sample in a single process. These and other advantages of the present invention will be readily apparent from the drawings, discussion and description which follow.

BRIEF DESCRIPTION OF THE INVENTION

There is disclosed herein an endometrial aspirator which comprises an aspirator tube which is a hollow, cylindrical body with an internal bore extending along its length. The aspirator tube includes a sampling end which is open and a notch defined through the tube. The notch begins at the sampling end of the tube and extends along a portion of the length of the tube. The aspirator further includes an aspirator piston which has a sealing portion configured to sealingly engage the internal bore of the tube. The piston further includes a cervical dilator portion which includes a base corresponding to the cross-section of the bore and which tapers from the base to form a tip. The dilator portion and the aspirator tube are configured so that the dilator portion is capable of being projected from the sampling end of the tube so as to facilitate insertion of the endometrial aspirator through a cervix and into a uterus. The aspirator further includes a piston rod coupled to the piston and operable to move the piston along the bore.

In particular embodiments, the aspirator tube includes a plurality of notches, each commencing at the sampling end of the tube and each extending along a portion of the length of the tube. In certain embodiments, the notches are undulating notches. In other embodiments, the bore may include a stop member proximate the second end of the tube for preventing the piston from being withdrawn from the second end, and may also include a stop member proximate the sampling end of the tube for preventing the piston from being withdrawn from the sampling end. The aspirator tube, aspirator piston and piston rod are all preferably fabricated from a flexible, polymeric material such as polypropylene, and the piston and piston rod may comprise a unitary, molded polymeric body. In a preferred embodiment, the aspirator tube has an outside diameter in the range of 2–5 millimeters, the dilator tip as a base diameter in the range of 2–4 millimeters and a tip diameter in the range of 0.5–1 millimeter. The aspirator tube preferably has a length in the range of 20–30 centimeters.

BRIEF DESCRIPTION OF THE DRAWINGS

FIG. 1 is a perspective view of one embodiment of endometrial aspirator structured in accord with the principles of the present invention;

FIG. 2 is a partial cross sectional view of a portion of the aspirator of FIG. 2 illustrating the two ends of the aspirator tube and the piston thereof;

FIG. 3 is a perspective view of one configuration of sampling end for an aspirator tube of the present invention;

FIG. 4 is a perspective view of another configuration of sampling end of an aspirator tube of the present invention; and FIG. 5 is a cross sectional view of a sampling end and piston of one embodiment of the present invention, illustrating the manner in which the aspirator functions as a cervical dilator.

DETAILED DESCRIPTION OF THE INVENTION

The present invention is directed to an endometrial aspirator which simplifies the sampling process, and maximizes the amount of sampled tissue, by eliminating the need for cutting of the sampling device in order to free the sample therefrom. The aspirator of the present invention is further configured to function as its own cervical dilator thereby eliminating a separate dilation step, and the use of additional apparatus. Referring now to FIG. 1, there is shown a perspective view of one embodiment of aspirator 10 structured in accord with the present invention. The aspirator 10 includes an aspirator tube 12 which is configured as a hollow, cylindrical body. The tube includes a sampling end 14 which is open and which further includes a notch commencing thereat and running along a portion of the length of the aspirator tube. As will be described further hereinbelow, the aspirator 10 includes a particularly configured piston therein, and the piston is connected to a piston rod 16, a portion of which is visible in FIG. 1. As further illustrated, a handle portion 18 is formed on the piston rod 16. The aspirator of the present invention is preferably fabricated from a flexible material, such as a synthetic, organic polymer. As illustrated in FIG. 1, the aspirator 10 may be bent to facilitate insertion and withdrawal. Although not illustrated, the aspirator may include a series of depth markings along the tube thereof to assist a physician in properly inserting the aspirator.

Referring now to FIG. 2 there is shown a cutaway view of a portion of the aspirator 10 of FIG. 1 and FIG. 2. The central portion of the aspirator is broken away, it being understood that it is generally similar those portions illustrated. FIG. 2 illustrates the aspirator tube 12 in cross section, and it will noted that the tube 12 is a hollow, cylindrical body having an internal bore relatively uniform cross section, extending along its length. As illustrated, the bore is of circular cross section, but it is to be understood that the bore may be of any other uniform cross sectional configuration. The aspirator tube includes a sampling end 14 which is an open end, and in this regard the aspirator of the present invention differs from prior art aspirators such as that of U.S. Pat. No. 5,069,224 which has a closed end and a side opening. The aspirator tube 12 further includes a notch 20 at the sampling end. The notch begins at the open end of the tube and extends through the tube and along a portion of the length of the tube 12. It has been found that the open ended tube of the present invention provides for superior sample collection and permits recovery of the entirety of the sample. The presence of the notch further enhances the function of the present invention.

FIG. 2 further illustrates the aspirator piston 22 of the sampler. The piston 22 includes a sealing portion 24 which engages the internal bore of the aspirator tube in a relatively gas tight manner. As illustrated in FIG. 2, the sealing portion 24 comprises a ring shaped portion of the piston 22. The piston 22 further includes a cervical dilator portion 26, and this portion includes a base generally corresponding to the cross section of the bore, and commencing at the sealing portion 24. The cervical dilator portion 26 tapers from the base to form a tip 28.

The aspirator 10 of the present invention includes a piston rod 16 which is connected to the piston 22 and functions to move the piston along the length of the bore. In the illustrated embodiment, the piston rod 16 and piston 22 are shown as being a unitary body, such as a body molded of a polymeric material, although, in some embodiments, the rod 16 and piston 22 may be separate elements, mechanically coupled together. As further illustrated in FIG. 1, handle portion 18 is connected to the piston rod 16 to assist in drawing the piston 22 through the bore. As illustrated, the handle 18 is a ring shaped handle, although it is to be understood that any other configuration of handle may be similarly employed. Further illustrated in FIG. 2 is a stop member 32 associated with the tube 12, at the second end 30 thereof. As illustrated, the stop member comprises a raised bead 32 extending along the second end 30, and this bead 32 permits inadvertent withdrawal of the piston 22 from the tube 12. As further illustrated in FIG. 2, the sampling end 14 of the tube 12 also includes a stop member 34, configured as an inwardly turned portion and prevents the piston from being fully withdrawn from the sampling end 14. Although the stops 32, 34 are not essential to the operation of the present invention, it is generally preferable that they be included to facilitate use of the device.

Referring now to FIG. 5, there is shown a cross sectional view of a portion of another aspirator of the present invention, illustrating the sampling end 14 of an aspirator tube 12, and further illustrating a piston 36, of slightly different design from that of FIG. 2. The piston 36 of the FIG. 5 embodiment differs from the piston 22 of the FIG. 2 embodiment primarily in the configuration of the sealing portion 38, which in the FIG. 5 embodiment is a relatively wide portion. It is to be understood that other configurations of sealing portion may be similarly employed in the present invention. For example, the sealing portion may comprise a series of rings or bands. FIG. 5 further illustrates the manner in which the piston 36 may be projected from the sampling end 14 of the tube 12. As illustrated, the stop member 34 prevents the piston from being pushed completely out of the bore. When the piston is projected as illustrated in FIG. 5, it operates in cooperation with the tube 12 to provide a tapered cervical dilator.

In use, the patient is prepared in accord generally accepted antiseptic techniques appropriate for an intrauterine procedure. The aspirator piston advanced through the bore of the tube so as to project from the sampling end, as in the FIG. 5 illustration, and the sampler is inserted into, and gently passed through the cervical canal and into the cavity of the uterus. If necessary, the tube may be lubricated with a water based lubricant to facilitate passage. Once the aspirator is properly positioned, the piston is withdrawal by means of the piston rod 16, so as to create a suction within the tube. The aspirator is then rotated and moved from side to side so as to sweep the surface of the uterine cavity. The configuration of the open ended of the tube, and in particular the notched, open ended tube functions to scrape endometrial tissue efficiently and gently. The collected tissue is drawn into the tube by the suction created by the piston. After the aspirator has been swept through the uterine cavity, it is withdrawn from the patient and the sample of tissue retained therein is discharged by simply pushing the piston back down through the tube. As will be seen, insertion, sample collection and sample discharge may simply be carried out by combined action of the particularly configured piston and tube. No additional equipment or steps are required.

Referring now to FIG. 3, there is shown a detailed, perspective view of one configuration of sampling end which may be employed in the practice of the present invention. The sampling end 14 of FIG. 3 includes two undulating notches which are diametrically opposed. FIG. 4 shows another configuration 40 of sampling end, which in this embodiment, is configured as series of five undulating notches. In the context of the present disclosure, an undulating notch is a notch with curving edges. It is to be understood that various other notch configurations may be similarly employed. For example, the aspirator may only include a single notch, and the notches need not be undulating, but may be square sided notches, tapered notches or otherwise configured notches.

The aspirator is preferably fabricated from a flexible material such as a polymeric material and polyproplylene comprises one particularly preferred polymer, although it is to be understood that other tissue compatible polymers such as fluoropolymers and the like may be similarly employed. The dimensions of the aspirator will be determined by the patient's anatomy. In general, the length of the aspirator tube will be in the range of 20–30 centimeters and its outside diameter in the range 2–5 millimeters. The base diameter of the dilator tip is generally in the range of 2–4 millimeters and the tip diameter in the range of 0.5–1 millimeter. The aspirator of the present invention may also be employed in veterinary practice, and dimensions will be scaled accordingly. It is to be understood that the foregoing drawings, discussion and description are merely meant to illustrate particularly embodiments of the present invention, and are not meant to be limitations of the practice thereof. It is the following claims, including all equivalents, which define the scope of the invention.

What is claimed is:

1. An endometrial aspirator comprising:

an aspirator tube configured as a hollow, cylindrical body, defining an internal bore, extending along the length thereof, said tube including a sampling distal end which is open, said tube further including a notch defined therethrough, said notch commencing at the sampling distal end of the tube and extending proximally along a portion of the length thereof;

an aspirator piston having a sealing portion configured to sealingly engage the internal bore of said aspirator tube, said piston having a cervical dilator portion which includes a base corresponding to the cross-section of said bore, said base providing said sealing portion, said dilator portion tapering distally from said base to form a tip, said dilator portion and aspirator tube being configured so that the dilator portion is capable of being projected from the sampling distal end of the tube so as to facilitate insertion of the endometrial aspirator through a cervix and into a uterus; and a piston rod coupled to the piston and operable to move the piston along said bore.

2. An aspirator as in claim 1, wherein said aspirator tube includes a plurality of notches defined therein, each notch commencing at the sampling distal end of the tube and extending proximally along a portion of the length thereof.

3. An aspirator as in claim 2, wherein said notches are undulating notches.

4. An aspirator as in claim 1, wherein said piston rod is sufficiently long so as to project from a second end of the aspirator tube, opposite the sampling distal end, when the dilator portion of the piston is projected from the sampling distal end of the tube.

5. An aspirator as in claim 4, wherein said bore includes a stop member disposed proximate the second end of the tube for preventing the piston from being withdrawn from said second end.

6. An aspirator as in claim 1, wherein said aspirator tube includes a stop member proximate the sampling distal end thereof for preventing the piston from being withdrawn from said sampling end.

7. An aspirator as in claim 1, wherein said aspirator tube, aspirator piston and piston rod are all fabricated from a flexible, polymeric material.

8. An aspirator as in claim 1, wherein said piston and piston rod comprise a unitary, molded. polymeric body.

9. An aspirator as in claim 8, wherein said unitary polymeric body is fabricated from polypropylene.

10. An aspirator as in claim 1, wherein said aspirator tube comprises a cylindrical body having an outside diameter in the range of 2 mm to 5 mm.

11. An aspirator as in claim 1, wherein said dilator tip has a base diameter in the range of 2 mm–4 mm and a tip diameter in the range of 0.5 mm to 1 mm.

12. An aspirator as in claim 1, wherein said aspirator tube has a length in the range of 20 cm to 30 cm.

13. An endometrial aspirator comprising aspirator tube configured as a hollow, cylindrical body having a length and the range of 20–30 cm, an outside diameter in the range of 2–5 mm and an inside diameter in the range of 2–4 mm, said tube including an open sampling distal end;

an aspirator piston having a scaling portion configured to sealingly engage the internal bore of the aspirator tube, said piston having a cervical dilator portion which includes a base corresponding to the cross section of the bore, said base providing said sealing portion, said dilator portion tampering distally from said base to form a tip, said tip having a diameter in the range of 0.5–1 mm, said dilator portion and aspirator tube being configured .so that the dilator portion is capable of being projected from the sampling distal end of the tube so as to facilitate insertion of the endometrial aspirator through a cervix and into a uterus; and a piston rod coupled to the piston and operable to move the piston along said bore.

\* \* \* \* \*